United States Patent [19]

Wollensak

[11] 3,931,298

[45] Jan. 6, 1976

[54] CHEMICAL PROCESS FOR FORMING 2,6-DIMETHYLANILINE

[75] Inventor: John C. Wollensak, Bloomfield Hills, Mich.

[73] Assignee: Ethyl Corporation, Richmond, Va.

[22] Filed: Sept. 20, 1974

[21] Appl. No.: 507,925

Related U.S. Application Data

[63] Continuation-in-part of Ser. No. 123,428, March 11, 1971, abandoned.

[52] U.S. Cl. ............................................... 260/581
[51] Int. Cl.² ............................................ C07C 85/02
[58] Field of Search ............ 260/575, 578, 580, 581

[56] References Cited
UNITED STATES PATENTS

| | | | |
|---|---|---|---|
| 2,013,873 | 9/1935 | Vogt | 260/581 |
| 2,413,598 | 12/1946 | Ballard et al. | 260/581 X |
| 3,037,057 | 5/1962 | Tinsley et al. | 260/578 |
| 3,219,702 | 11/1965 | Van Verth et al. | 260/571 |
| 3,219,704 | 11/1965 | Wilder et al. | 260/576 |
| 3,272,865 | 9/1966 | Barker | 260/581 |
| 3,278,598 | 10/1966 | Markiewitz | 260/581 X |
| 3,442,950 | 5/1969 | Barker | 260/578 X |

FOREIGN PATENTS OR APPLICATIONS

| | | | |
|---|---|---|---|
| 251,334 | 10/1912 | Germany | 260/578 |
| 22,517 | 1/1962 | Germany | 260/580 |

*Primary Examiner*—Allen B. Curtis
*Attorney, Agent, or Firm*—Donald L. Johnson; Robert A. Linn; Joseph D. Odenweller

[57] ABSTRACT

Hydroxy aromatics are aminated to form the corresponding aromatic amine by reaction at 200°–400°C with ammonia in the presence of a cyclohexanone and water in contact with a hydrogen transfer catalyst. For example, 2,6-dimethylphenol reacts with ammonia in the presence of cyclohexanone, water and a supported palladium catalyst to form 2,6-dimethylaniline.

25 Claims, No Drawings

CHEMICAL PROCESS FOR FORMING 2,6-DIMETHYLANILINE

This application is a continuation-in-part of application Ser. No. 123,428, filed Mar. 11, 1971 now abandoned.

BACKGROUND

Aromatic amines such as aniline are useful in a variety of applications, such as in the preparation of dyes, herbicides and as antiknock agents for spark-ignited gasoline powered internal combustion engines. In the past, they have been prepared by reducing nitro aromatics, such as nitrobenzene. This is a very useful method of preparation, but depends upon the ready availability of the proper nitro aromatic which, in some cases, is not available. Another method is described by Van Verth et al, U.S. Pat. No. 3,219,702, wherein a cyclohexanone is reacted with an ammonia compound in the presence of a hydrogen acceptor (e.g., a nitrobenzene) and a dehydrogenation catalyst. Since the main reactant in this process is a cyclohexanone, its utility depends upon the availability of the appropriate cyclohexanone.

In Wilder et al, U.S. Pat. No. 3,219,704, a similar process is described which differs in the omission of the hydrogen acceptor and the requirement of an amount of the cyclohexanone at least equivalent to the amount of ammonia compound present.

Another process is described in Barker, U.S. Pat. No. 3,272,865, which involves the reaction of a hydroxybenzene with ammonia or amine in contact with a silica-alumina, titania-alumina, zirconia-alumina, phosphoric acid or tungsten oxide catalyst. This process is quite similar to that described by Neuroessen, in U.S. Pat. No. 1,935,209, and by Lowy et al, in U.S. Pat. No. 1,449,423.

In Barker, U.S. Pat. No. 3,442,950, another process is described involving the reaction of a cyclohexanol with an aminating agent in the presence of a catalyst. If cyclohexanone is present in the cyclohexanol, hydrogen must be added in an amount at least sufficient on a molar basis to convert the cyclohexanone to cyclohexanol.

Other processes for making aromatic amines are taught by Ballard, U.S. Pat. No. 2,413,598; Vogt, U.S. Pat. No. 2,013,873; Groggins, "Unit Processes in Organic Synthesis," 5th Edition; and Houben-Weyl, "Methoden der Organische Chemie," Vol. 11/1, pages 117–122.

SUMMARY

The present process comprises a process for converting hydroxy-substituted aromatic compounds to the corresponding aromatic amine by reacting the aromatic hydroxy compound with ammonia in the presence of a catalytic amount of a cyclohexanone and in contact with a hydrogen transfer catalyst, most preferably palladium. A major advantage of the present process is that it allows the preparation of aromatic amines from readily available inexpensive hydroxy aromatics, such as the preparation of aniline from phenol, 2,6-dimethylaniline from 2,6-dimethylphenol, and naphthyl amines from naphthols.

DESCRIPTION OF THE PREFERRED EMBODIMENTS

A preferred embodiment of this invention is a process for converting hydroxy-substituted aromatics to the corresponding amino-substituted aromatics, said process comprising reacting a hydroxy-substituted aromatic with ammonia in the presence of a hydrogen transfer catalyst at a temperature of from about 200°–400°C.

Since the reaction of certain hydroxy aromatic starting materials with ammonia in the presence of other catalyst systems to form aromatic amines is known, the present invention can be viewed as an improvement in this process wherein the catalyst employed is a hydrogen transfer catalyst, such as palladium in combination with a cyclohexanone co-catalyst.

The process of this invention is generally applicable to a broad range of hydroxy aromatics. By "hydroxy aromatic" is meant a compound containing at least one benzene ring to which at least one hydroxy group is bonded. These include the simple hydroxy aromatics in which the aromatic portion of the compound contains only six-membered carbocyclic rings, such as benzene, naphthalene, anthracene, and the like, which are referred to herein collectively as phenols. It also includes complex hydroxy aromatics in which a heterocyclic ring is fused to a hydroxy-substituted benzene ring represented by benzofuran, indole, and the like, which are referred to herein collectively as heterocyclic phenols. Since the only reaction site involves the hydroxyl group bonded to a benzene ring, the rest of the hydroxy aromatic can be anything as long as it does not contain substituents which would interfere with the course of the reaction, for example, by reacting with the aminating agent. The aryl portion of the molecule may be a mono-, di- or tri-nuclear radical, or for that matter, can contain even more aryl groups. As stated above, the aryl portion of the hydroxy aromatic may also be fused to other cyclic systems including heterocyclic systems, such as those containing cyclo oxygen, nitrogen and sulfur rings. For example, the hydroxy aromatic can be any of the isomeric hydroxy-substituted derivatives of benzene, naphthalene, anthracene, phenanthrene, indene, isoindene, benzofuran, isobenzofuran, thionaphthene, indole, isoindole, indolenine, 2-isobenzazole, 1,2-benzodiazole, 1,3-benzodiazole, indiazene, 1,3-benzisodiazole, 1,2,3-benzotriazole, benzisoxazole, benzoxadiazole, 1,2-benzopyran, 1,4-benzopyran, quinoline, isoquinoline, 1,3-benzodiazine, 1,2-benzisoxazine, acenaphthene, fluorene, dibenzopyrrole, xanthene, thianthrene, phenothiazine, phenoxazine, naphthacene, chrysene, pyrene, triphenylene, and the like, wherein the hydroxyl group is bonded to a nuclear carbon atom. Representative examples of these are: naphthol-1, 1-hydroxy anthracene, 2-hydroxy phenanthrene, 7-hydroxy indene, 6-hydroxy isoindene, 7-hydroxy benzofuran, 6-hydroxy isobenzofuran, 4-hydroxy thionaphthene, 7-hydroxy indole, 5-hydroxy isoindole, 4-hydroxy isoindolenine, 7-hydroxy-2-isobenzoxazole, 4-hydroxy-1,2-benzodiazole, 7-hydroxy-1,3-benzodiazole, 7-hydroxy indiazene, 4-hydroxy-1,3-benzisodiazole, 4-hydroxy-1,2,3-benzotriazole, 4-hydroxy benzisoxazole, 7-hydroxybenzoxadiazole, 8-hydroxy-1,2-benzopyran, 5-hydroxy-1,4-benzopyran, 8-hydroxy quinoline, 5-hydroxy isoquinoline, 7-hydroxy-1,3-benzodiazine, 5-hydroxy-1,2-benzisoxazine, 4-hydroxy acenaphthene, 1-hydroxy fluorene, 4-hydroxy dibenzopyrrole, 1-hydroxy xanthene, 1-hydroxy thianthrene, 4-hydroxy phenoxazine, 1-hydroxy naphthacene, 1-hydroxy chrysene, 2-hydroxy pyrene, 2-hydroxy triphenylene, and the like.

The process is also applicable to aryl hydroxy compounds having more than one hydroxyl radical bonded to a nuclear aromatic carbon atom. For example, the process can be applied to such polyhydroxy aromatics as hydroquinones, resorcinols, catechols, 1,3-dihydroxy naphthalenes, pyrogallols, phloroglucinols, and the like.

Substituents other than hydroxyl groups may be present in the aromatic compounds as long as they do not interfere with the course of the reaction. That is to say, the other substituents should be relatively inert to ammonia and hydrogen and should not act to poison the hydrogen transfer catalyst. For example, any of the previously-listed aromatics may be substituted in a variety of positions with alkyl radicals, aralkyl radicals, cycloalkyl radicals, chlorine, bromine, iodine, fluorine, and the like. A few representative examples of these using the simpler aromatic structure are p-chlorophenol, 2,6-dimethyl-4-chlorophenol, β-bromo-α-naphthol, β-chloro-7-hydroxy-coumarone, 2-acetoxy-7-hydroxy-indolenine, 3-n-dodecyl-7-hydroxy-benzisoxazole, 8-hydroxy-1,2-benzopyran, 7-sec-octadecyl-8-hydroxy-isocoumarin, and the like.

Of the above hydroxy aromatics, the preferred starting materials are those in which the aromatic portion is a hydrocarbon containing at least one benzene ring to which at least one hydroxy group is bonded.

The reaction proceeds very well when the hydroxy aromatic is a mononuclear phenol sometimes called hdyroxy-substituted benzene. As previously, these phenol-type materials can be substituted with other groups as long as they do not interfere with the course of the reaction. A preferred class of such hydroxy-substituted benzenes are those having the formula:

I wherein $n$ is an integer from 0–3, $m$ is an integer from 1–3, and R is selected from the group consisting of aliphatic alkyl radicals containing from 1–50 carbon atoms, aralkyl radicals containing from 7–20 carbon atoms and cycloalkyl radicals containing from 6–20 carbon atoms. Some examples of these are: phenol, catechol, resorcinol, pyrogallol, phluoroglucinol, hydroquinone, 3,5-di-tert-butylphenol, 2,6-di-tert-butylhydroquinone, 3-methylcatechol, p-cresol, m-cresol, p-pentacontyl phenol, 2,4-didodecyl phenol, p-cyclohexyl phenol, 3-cyclooctyl phenol, p-(4-sec-dodecylcyclohexyl)phenol, 2,4,6-trimethyl phluoroglucinol, m-sec-eicosyl phenol, p-(4-tert-tridecylbenzyl)phenol, 4-(3,5-di-sec-heptylcyclohexyl)phenol, and 2-sec-pentacontyl hydroquinone. Of the above, the preferred reactants are the mononuclear alkyl-substituted phenols.

The advantages of the process over the prior art methods display themselves to a greater extent when the hydroxy-substituted benzene is a mononuclear phenol in which at least one nuclear position ortho to the phenolic hydroxyl group is substituted with a radical selected from the group consisting of alkyl radicals containing from 1–50 carbon atoms, mononuclear aryl radicals containing from 6–20 carbon atoms, cycloalkyl radicals containing from 6–20 carbon atoms and primary and secondary aralkyl radicals containing from 7–20 carbon atoms. These are phenols having the formula:

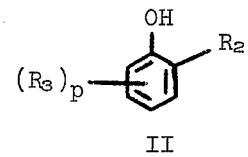

II wherein $p$ is an integer from 0–2, $R_2$ is selected from the group consisting of alkyl radicals containing from 1–50 carbon atoms, aralkyl radicals containing from 7–20 carbon atoms, mononuclear aryl radicals containing from 6–20 carbon atoms and cycloalkyl radicals containing from 6–20 carbon atoms, and $R_3$ is selected from the group consisting of alkyl radicals containing from 1–50 carbon atoms, aralkyl radicals containing from 7–20 carbon atoms, mononuclear aryl radicals containing from 6–20 carbon atoms, and cycloalkyl radicals containing from 6–20 carbon atoms. Some examples of these phenolic starting materials are:
o-sec-butylphenol,
2,5-dimethylphenol,
o-tert-butylphenol,
o-tert-amyl-p-cresol,
o-sec-pentacontylphenol,
o-ethylphenol,
2,4,6-tri-sec-butylphenol,
2,4-dimethylphenol,
4-(α,α-dimethylbenzyl)-o-cresol,
2-(α-methylbenzyl)phenol,
2-cyclohexyl-p-cresol,
2-cyclooctyl-p-cresol,
2-(3,5-di-tert-butyl-cyclohexyl)-4-sec-eicosylphenol,
2-sec-pentacontylphenol,
2-(α-methyl-4-dodecylbenzyl)phenol,
2-phenylphenol,
2-(4-tetradecylphenyl)phenol,
2-(3,5-di-sec-heptylphenyl)phenol,
2-triacontylphenol,
2-isopropylphenol,
2,4-di-sec-dodecylphenol, and
2-(α-methyl-4-sec-amylbenzyl)phenol.

An especially valuable feature of this invention is its ability to replace an aromatic hydroxyl radical with an amine radical when both positions on the aromatic nucleus ortho to the hydroxyl group are substituted. This cannot be readily done using prior art methods. When the aromatic hydroxy compound is a mononuclear phenol the phenolic reactant used in this embodiment of the invention has the formula:

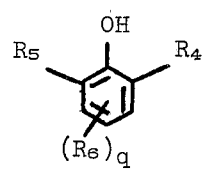

III wherein $q$ is 0 or 1, and $R_4$ and $R_5$ are selected from the same group as $R_2$ in Formula II, and $R_6$ is selected from the same group as $R_3$ in Formula II. Some examples of these phenols are:

2-methyl-6-tert-butylphenol,
2,6-dimethylphenol,
2,4,6-trimethylphenol,
2,6-di-sec-butylphenol,
2,6-di-sec-butyl-p-cresol,
2,6-di-tert-butylphenol,
2,4-dimethyl-6-sec-butylphenol,
2,6-diisopropylphenol,
2,6-di-sec-octylphenol,
2,6-di($\alpha$-methylbenzyl)phenol,
6-($\alpha$-methylbenzyl)-o-cresol,
2,4-di-methyl-6-(2,3-benzobenzyl)phenol,
2-(3-tert-butyl-5-isopropylbenzyl)phenol,
2-cyclooctyl-6-ethylphenol,
2,6-dibornylphenol,
2,6-dicyclohexylphenol,
2-methyl-6-($\alpha,\alpha$-dimethylbenzyl)phenol,
6-sec-pentacontyl-o-cresol,
2,4-dimethyl-6-docosylphenol,
6-phenol-o-cresol,
2,4-dimethyl-6-(4-tetradecylphenyl)phenol,
2-ethyl-6-(3,5-diheptylphenyl)-p-cresol, and the like.

The amount of ammonia added is not critical. On a mole basis it may be less than the hydroxy aromatic or it may be an excess of the hydroxy aromatic. This does not affect the operability of the process but only the optimization of yield. In general, it is preferred to use a molar excess of ammonia. A useful range based on hydroxy aromatic is from about 0.5–50 moles of ammonia per mole of hydroxy aromatic. A preferred range is from 1–10 moles of ammonia per mole of hydroxy aromatic.

It is essential that the reaction mixture contain a catalytic amount of a cyclohexanone. Without this the reaction does not proceed to give the herein-described results. Although extremely small amounts will cause the reaction to proceed, it has been found that, in general, the reaction proceeds at a satisfactory rate when the initial mixture prior to adding ammonia contains at least about 0.05 mole of a cyclohexanone per mole of hydroxy aromatic. There is no critical upper limit, but for economic reasons, a most useful range is from about 0.1 to about 0.5 mole of cyclohexanone per mole of hydroxy aromatic. This is because only very small amounts, if any, of the cyclohexanone catalyst component are converted to the aromatic amine product.

When ammonia is added to the reaction mixture containing the hydrogen-transfer catalyst and the cyclohexanone co-catalyst and the mixture heated a number of complex reactions ensue, the nature of which is not completely understood. It is known from analysis of the reaction mixture that a number of materials referred to collectively as "reduced products" are formed. By "reduced products" is meant the group of compounds which contain a saturated cyclohexyl ring and correspond in structure to the cyclohexanone co-catalyst. These include the corresponding derivatives of cyclohexanol and cyclohexyl amine. The cyclohexanone is the major constituent of these reduced products and, for that reason, they are collectively referred to herein as cyclohexanones, but it should be understood that this term as used herein includes the other reduced products which exist in equilibrium with cyclohexanone under the actual reaction conditions. The nature of this equilibrium and the reduced products will be discussed in more detail later.

The cyclohexanone used as the co-catalyst can be any compound containing a saturated six-membered cycloaliphatic ketone in its structure. The cyclohexanone co-catalyst can correspond in structure with the cyclohexanone which would form by partial reduction of the hydroxy aromatic compound or it can be an entirely different cyclohexanone. Although not bound by any theory as to how the process operates, it is believed that the cyclohexanone co-catalyst functions by forming an imine derivative with the aminating agent which then transfers hydrogen to the hydroxy aromatic, forming an aromatic amine and regenerating cyclohexanone co-catalyst, thus making the reaction self-propagating. Hence, no matter what cyclohexanone compound is added initially to start the reaction, the cyclohexanone present after the reaction is under way will correspond in structure to that of the partially reduced hydroxy aromatic compound. This series of reactions can be illustrated by the following equations in which phenol represents the hydroxy aromatic.

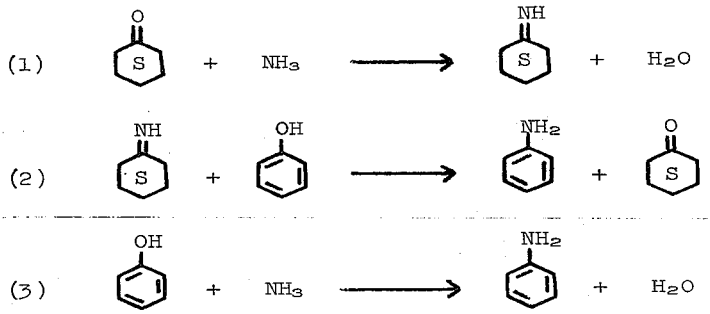

The result of the above is that the cyclohexanone consumed in reaction (1) is regenerated by reaction (2), and the cyclohexylimine formed in reaction (1) is consumed in reaction (2). The net result is represented by reaction (3): the hydroxy aromatic group attached to the aromatic group is replaced with an amine group. Whatever the mechanism, the results are that only a catalytic amount of the cyclohexanone is required to initiate the reaction and the hydroxy aromatic is aminated by the ammonia.

As discussed above, both cyclohexanols and cyclohexyl amines have been found in the reduced products present during the reaction. It is believed that the above is still a good overall representation of how the process converts the hydroxy aromatic to the corresponding aromatic amine and that the other identified reduced products, such as cyclohexanols and cyclohexyl amines, are in redox equilibrium with the cyclohexanone co-catalyst due to the presence of the hydrogen transfer catalyst. However, the successful practice of the novel process described herein does not require an understanding of its exact mechanism.

Van Verth et al, U.S. Pat. No. 3,219,702, and Wilder et al, U.S. Pat. No. 3,219,704, disclose a process for making aromatic amines by reacting a cyclohexanone with ammonia using a palladium catalyst. Although this reaction may proceed to some small extent during operation of the present process, it represents, at most, but a minor side reaction. In the present process the aromatic amine is formed from the hydroxy aromatic. The following examples demonstrate this most conclusively.

EXAMPLE 1

This example shows that the amount of reduced products remains substantially the same as the reaction proceeds and that the phenol is converted to an aniline.

In an autoclave was placed 164 grams of 2-methyl-6-tert-butylphenol, 176 grams of 29% aqueous ammonia and 9.5 grams of 5% palladium on charcoal. This was pressurized to 500 psig with hydrogen and heated to 200°C and then pressurized to 1000 psig with hydrogen. After a pressure drop of 920 psig, due to reduction of a portion of the 2-methyl-6-tert-butylphenol, the autoclave was cooled to room temperature and vented. It was again sealed and heated to 250°C and stirred at this temperature for 15 hours. Samples were periodically withdrawn and analyzed to follow the course of the reaction. The results are shown in the following table.

| Reaction time[1] | % Reduced Products[2,3] | % Phenol[2] | % Aniline[2] |
|---|---|---|---|
| start | 20.2 | 72.2 | 1.9 |
| 2 hrs | 29.0 | 37.5 | 26.6 |
| 6.2 hrs | 25.4 | 20.0 | 43.8 |
| 8.5 hrs | 23.4 | 15.5 | 49.3 |
| 15 hrs | 19.0 | 15.7 | 52.4 |

[1]From the time the autoclave was heated to 250°C.
[2]As the 2-methyl-6-tert-butyl derivative.
[3]Mainly 2-methyl-6-tert-butylcyclohexanone plus lesser amounts of the corresponding cyclohexanol and cyclohexylamine.

The above results show that the net result of the reaction is the consumption of the phenolic starting material and the production of the aromatic amine product. The amount of cyclohexanone (i.e., "reduced products") stays about the same during the reaction, which serves to support the above postulated mechanism and clearly distinguishes the present process from that described by Van Verth et al or Wilder et al.

As stated previously, the cyclohexanone co-catalyst component is essential to the process. This is shown in the following examples.

EXAMPLE 2

Reaction with Cyclohexanone Co-Catalyst

In the autoclave used in Example 1 was placed 164 grams of 2-methyl-6-tert-butylphenol and 9.6 grams of 5% palladium on charcoal. This was partially hydrogenated at 193°C and 500 psig hydrogen to form the reduced products containing the cyclohexanone co-catalyst. Then 188 grams of 27% aqueous ammonia was added and the amination reaction carried out at 250°C for 8 hours 10 minutes. The organic phase of the mixture was analyzed following the hydrogenation and again at the end of the reaction period. The results were as follows.

| Component | After Hydrogenation | End of Reaction |
|---|---|---|
| reduced products | 25.22% | 19.21% |
| 2-methyl-6-tert-butylphenol | 70.52% | 12.15% |
| 2-methyl-6-tert-butylaniline | 0% | 59.31% |

EXAMPLE 3

Reaction without Cyclohexanone Co-Catalyst

This reaction was carried out as in Example 2 but without the initial hydrogenation to form the reduced products.

In an autoclave was placed 164 grams of 2-methyl-6-tert-butylphenol, 176 grams of 29% aqueous ammonia and 9.5 grams of 5% palladium on charcoal. The autoclave was flushed with nitrogen, sealed, and heated to 250°C and stirred at that temperature for 8 hours. The composition of the organic phase before and after the 8 hour reaction period was as follows.

| | Before Reaction | End of Reaction |
|---|---|---|
| 2-methyl-6-tert butylphenol | 100% | 94.4% |
| 2-methyl-6-tert-butylcyclohexanone | 0% | 0% |
| 2-methyl-6-tert-butylaniline | 0% | 0% |

The small loss of 2-methyl-6-tert-butylphenol in Example 3 was probably due to slight thermal dealkylation. By comparing Example 2 with Example 3 it is apparent that the cyclohexanone co-catalyst is a critical component of the process which enables it to aminate the hydroxy aromatic.

EXAMPLE 4

This example shows the necessity of having a phenol present to be aminated and that without the phenol only very small amounts of aromatic amine are formed.

In an autoclave was placed 164.3 grams of 2-methyl-6-tert-butylphenol and 9.6 grams of 5% palladium on charcoal. This was pressurized to 1,470 psig with hydrogen and heated to 150°C. Pressure dropped to zero and the autoclave was repressurized to 1195 psig with hydrogen. After 70 minutes of hydrogenation the autoclave was cooled and vented. Its contents analyzed by VPC as 98.2% 2-methyl-6-tert-butyl cyclohexanone plus four unidentified components in small amount. There was no measurable 2-methyl-6-tert-butylphenol.

To the above was added 188 grams of 29% aqueous ammonia and the vessel sealed and heated to 250°C and held at that temperature for 8 hours. The autoclave was then cooled and the reaction mixture analyzed by VPC as follows:

| | |
|---|---|
| 2-methyl-6-tert-butyl cyclohexanone | 62.1% |
| 2-methyl-6-tert-butyl cyclohexylamine | 20.9% |
| 2-methyl-6-tert-butyl aniline | 12.5% |
| 1-methyl-3-tert-butyl benzene | 1.5% |
| 2-methyl-6-tert-butylphenol | 1.5% |

Comparing these results with Example 2 clearly shows the criticality of having both the phenol and the cyclohexanone co-catalyst present in order to have the reaction proceed as described.

As stated above, any cyclohexanone can be used to initiate the reaction. Cyclohexanones corresponding in structure to the partially reduced hydroxy aromatic are preferred. For example, the cyclohexanone of partially reduced phenol is the compound cyclohexanone. Likewise, the partially reduced alkylated hydroxybenzenes are the alkylated cyclohexanones. The following examples serve to illustrate what is meant by the cyclohexanone corresponding in structure to the partially reduced hydroxy aromatics.

| Hydroxy Aromatic | Cyclohexanone Corresponding in Structure to Partially Reduced Hydroxy Aromatics |
|---|---|
| 2,6-dimethylphenol | 2,6-dimethylcyclohexanone |
| o-cresol | 2-methylcyclohexanone |
| 2-methyl-6-tert-butyl-phenol | 2-methyl-6-tert-butyl-cyclohexanone |
| 2,6-diisopropylphenol | 2,6-diisopropylcyclohexanone |
| 2,4-dimethylphenol | 2,4-dimethylcyclohexanone |
| 2,4,6-trimethylphenol | 2,4,6-trimethylcyclohexanone |
| 2,6-diisopropylphenol | 2,6-diisopropylcyclohexanone |
| 2,6-di-sec-butylphenol | 2,6-di-sec-butylcyclohexanone |
| o-sec-butylphenol | 2-sec-butylcyclohexanone |
| α-naphthol | 2,3-benzocyclohexanone |

The cyclohexanone co-catalyst need not be added as such at the start of the process but can be formed in situ by adding a small amount of a reducing agent. Hence, a highly preferred embodiment of the invention is a process for converting hydroxy-substituted aromatics to amino-substituted aromatics, said process comprising reacting a hydroxy-substituted aromatic with ammonia in the presence of a catalytic amount of a cyclohexanone formed in situ by adding an amount of a reducing agent sufficient to reduce a small amount of said hydroxy-substituted aromatic to said catalytic amount of a cyclohexanone, in contact with a hydrogen transfer catalyst at a temperature of from about 200°–400°C.

The reducing agent employed can be any of those known to be capable of reducing a hydroxy aromatic to the corresponding cyclohexanone. One such group of useful reducing agents is the hydroaromatics. These are compounds containing a 6-membered cycloaliphatic structure which can lose hydrogen and form an aromatic compound (Fieser and Fieser, *Advanced Organic Chem.*, p. 645, Reinhold Publishing Co., N.Y., 1961). Some typical examples of these are: decalin, tetralin, cyclohexane, cyclohexanol, and the like. Other organic reducing agents such as hydroquinone, catechol, and the like, can also be used. Compounds that form hydrogen in contact with water are also useful. These include sodium aluminum hydride, sodium borohydride, calcium hydride, lithium aluminum hydride, and the like.

As mentioned earlier, both cyclohexanols and cyclohexyl amines have been identified in the reduced products. These components in the presence of a phenol and a hydrogen transfer catalyst can form the cyclohexanone co-catalyst. Accordingly, either cyclohexanols or cyclohexyl amines can be added to the phenol starting material to form the required cyclohexanone co-catalyst.

The most preferred reducing agent is hydrogen. Thus, the reaction can be initiated by adding a small amount of hydrogen to the reaction mixture sufficient to reduce some of the hydroxy aromatic to form at least a catalytic amount of the cyclohexanone as previously described. Once the cyclohexanone catalyst has formed no additional reducing agent is required. The amount of hydrogen added should be at least enough to form 0.05 mole of a cyclohexanone per mole of hydroxy aromatic. An excess is generally employed because it does not all react. The formation of the cyclohexanone catalyst can be readily accomplished by adding the hydroxy aromatic and hydrogen transfer catalyst to a reaction vessel and then pressurizing the vessel with about 10–500 psig of hydrogen and heating the mixture to about 200°C until sufficient hydrogen has been reacted to form the catalyst. Following this, water and ammonia can be added and the process completed. This is referred to as the two-stage process. If desired, the water and ammonia can be added prior to the reduction. A very facile method of carrying out the process is to place the hydroxy aromatic, aqueous ammonia and hydrogen transfer catalyst in the reaction vessel and then pressurize the vessel with hydrogen while stirring at reaction temperature.

The hydrogen transfer catalyst can be any of the well-known hydrogenation-dehydrogenation catalysts, although they all do not give equivalent results. Some examples are platinum, palladium, copper chromite, chromium oxide, and the like. Preferably, the catalysts are supported on a suitable support such as alumina, silica, silica-alumina, magnesia, zirconia, titania, charcoal, and the like. Examples include alumina-chromia, magnesia-chromia, alumina-molybdena, alumina-vanadia, alumina-vanadia-zinc oxide, alumina-urania, alumina-tungstate, alumina-palladium, alumina-copper-palladium, and the like.

Preferably, the catalyst is a Group VIII metal-containing catalyst such as nickel, palladium, platinum, cobalt, rhodium, iridium, ruthenium, osmium, and mixtures thereof.

The most preferred catalyst is palladium on a suitable support such as charcoal. Palladium has been found to give vastly superior results. The amount of catalyst need only be sufficient to catalyze hydrogen exchange during the reaction. Good results are obtained using from about 1 to 10 parts by weight of hydrogen transfer catalyst (excluding support) per 1,000 parts of reaction mixture.

It has been found that the initial reduction to form the cyclohexanone co-catalyst does not proceed at a reasonable rate if the reaction mixture contains ammonia unless water is also present in the mixture. A useful range of water is from about 25 to 500 parts by weight per 1,000 parts of reaction mixture. The water can be separately added or it can be added together with the aminating agent forming an aqueous aminating solution.

Although a solvent is not required in the process, the use of a solvent is not detrimental. Preferred solvents are liquid hydrocarbons boiling in the range of from about 50°–200°C. Useful examples include hexane, heptane, octane, nonane, decane, benzene, toluene, xylene, and the like.

The reaction proceeds at elevated temperatures of from about 175°–500°C. A preferred operating temperature is from about 200°–400°C.

The process can be carried out as a batch or continuous operation. In a batch operation the hydroxy aromatic, cyclohexanone catalyst, ammonia, water and hydrogen transfer catalyst can be merely mixed together and heated in a sealed vessel to reaction temperature. This is referred to as the one-stage process. Amination is usually optimum in 4–12 hours. Optionally, the hydroxy aromatic, cyclohexanone catalyst, water and hydrogen transfer catalyst can be mixed in a closed vessel, heated to reaction temperature and then ammonia added over an extended period of time. In still another mode of operation the hydroxy aromatic, hydrogen transfer catalyst and water can be placed in a reaction vessel together with a small amount of a reducing agent such as tetralin. This mixture is then heated, causing the formation of a catalytic amount of the cyclohexanone catalyst corresponding in structure to the hydroxy aromatic, following which the ammonia is added and the reaction completed.

A simple method of carrying out the process is to merely place the hydroxy aromatic, hydrogen transfer catalyst, aqueous ammonia and hydrogen in a pressure reaction vessel and heat to reaction temperature while stirring.

In the continuous method the hydroxy aromatic, cyclohexanone, water and ammonia are passed through a fixed bed hydrogen transfer catalyst maintained at reaction temperature at a space velocity such that the residence time is sufficient to provide a good conversion to aromatic amine. In one version of the continuous process a mixture of hydroxy aromatic, ammonia, water and hydrogen is passed through the fixed bed catalyst which causes the cyclohexanone catalyst to form in situ, which in turn catalyzes the amination reaction on the aromatic hydroxy compound.

In another variation of the above-mentioned in situ catalyst formation method the hydroxy aromatic and hydrogen transfer catalyst are placed in a sealed reaction vessel which is then pressurized with from about 10–500 psig with hydrogen and heated until a catalytic amount of a cyclohexanone forms. Following this, the water and ammonia are added and the reaction completed. This is the two-stage process previously referred to. The partial hydrogenation of the hydroxy aromatic to form reduced products containing the cyclohexanone co-catalyst is conducted prior to adding the ammonia. At this stage the reduced products have been found to contain a large amount of cyclohexanone and the remainder mainly the corresponding cyclohexanol in equilibrium with it. This avoids any deactivating effect the ammonia might have on the hydrogen transfer catalyst. According to this most preferred method the hydroxy aromatic and a supported palladium hydrogen transfer catalyst are first charged to the reaction vessel. The reaction rate is dependent upon the amount of catalyst used. Good results are obtained using from about 0.001 to about 0.01 mole of palladium per mole of hydroxy aromatic. Charcoal is an excellent support for the palladium. Catalyst loadings of 1–10 per cent palladium are very effective. The reaction vessel is then sealed, flushed with nitrogen, and then pressurized with hydrogen to effect partial reduction. The hydrogen pressure used is not critical so long as it suffices to cause hydrogenation. Pressures of about 10–500 psig are useful.

Reaction rate in the subsequent amination stage is dependent upon the amount of cyclohexanone co-catalyst formed in the first stage. Since the cyclohexanone itself is a catalyst and is not converted in any substantial amount to the desired aromatic amine (cf. Examples 1–4), it is counter-productive to use too much cyclohexanone co-catalyst. An economic balance should be reached between reaction rate and amount of product produced. Thus, the amount of hydrogen used in the first stage should be that amount which will form the optimum amount of cyclohexanone co-catalyst. As mentioned earlier, a useful range is about 0.05 to about 0.5 mole of the particular cyclohexanone per mole of hydroxy aromatic remaining in the hydrogenated mixture. Since two moles of hydrogen are required to reduce one mole of hydroxy aromatic to the corresponding cyclohexanone, this requires in the range of 0.1 to 1.0 mole of hydrogen per mole of cyclohexanone co-catalyst to be produced.

Hydrogenation is then carried out at a temperature which is adequate to promote the reduction. This will vary somewhat with the amount of palladium catalyst and its activity. The hydrogenation generally initiates at temperatures below about 100°C, but if it does not, the mixture can be merely heated further under hydrogen pressure until hydrogen uptake occurs. It is seldom necessary to heat over about 200°C.

After the hydrogenation has progressed to the desired degree the reaction mixture which now contains the desired amount of a cyclohexanone as a major constituent of the reduced products formed in the hydrogenation is cooled and residual hydrogen vented. At this time, the second stage of the reaction is conducted. This is the amination stage. Ammonia is added to the reaction vessel in the amounts previously described. In this two-stage embodiment a most preferred amount of ammonia is about 1–4 moles per mole of hydroxy aromatic originally charged to the reaction vessel prior to reduction. Thus, a typical reactor content at the start of the amination stage would be about 0.8 mole of hydroxy aromatic, 0.2 mole of the corresponding reduced products (mainly a cyclohexanone), 0.005 mole of palladium on a charcoal support, and about 1–4 moles of ammonia.

The amination reaction will proceed without adding water, so the use of water is not critical. However, the reaction rate is increased by including water in the system. Improved results are obtained when the system includes about 0.5–10 moles of water per mole of initial hydroxy aromatic. A preferred range is about 1–4 moles of water per mole of initial hydroxy aromatic. A facile method of carrying out the process is to add the water and ammonia together as an aqueous ammonia solution. This makes the handling of ammonia much easier. By adjusting the ammonia concentration the proper amount of ammonia and water can be added concurrently.

The reaction rate is temperature dependent. As mentioned earlier, a preferred operating range for the amination is about 200°–400°C. Excellent results are obtained at about 225°–275°C. If the hydroxy aromatic starting material contains tert-alkyl substituents the temperature should not be increased above about 275°C for any extended period or dealkylation will occur.

As discussed above, the reaction rate is dependent upon a number of variables, so there is no fixed time in which the amination should be conducted. Although the amination is usually optimized in about 4–12 hours, it has been found that under the most preferred conditions the optimum yield can be obtained in only 1–2 hours.

Product is generally recovered by distillation. Unreacted ammonia, reduced products and hydroxy aromatic can be recycled. The following examples serve to illustrate the manner in which the process may be conducted. All parts are by weight unless otherwise stated.

EXAMPLE 5

In a pressure reaction vessel was placed 0.55 mole parts of 2-methyl-6-tert-butylphenol, 0.55 mole parts of 2-methyl-6-tert-butylcyclohexanone, 0.0045 mole parts of palladium (5 weight per cent on charcoal support) and 3 mole parts of ammonia. The vessel was sealed and, while stirring, heated to 250°C. (Water was not added in this example because the initial reaction of ammonia with cyclohexanone produced 0.55 mole part of water.) The mixture was stirred at this temperature for 3 hours and then cooled and distilled, giving a 46.8 per cent conversion to 2-methyl-6-tert-butyl aniline. The yield of 2-methyl-6-tert-butyl aniline based on consumed phenol was about 98 per cent.

EXAMPLE 6

In a pressure reaction vessel was placed one mole part of 2-methyl-6-tert-butylphenol and 0.0047 mole part of palladium (5 weight per cent on charcoal support). The vessel was pressurized with hydrogen to 300 psig and stirred at 200°C for 3.5 hours. (Total pressure drop 2,150 psi.) Then, 3 mole parts of ammonia were added and the vessel sealed and stirred at 250°C for 25 hours. Following this, 6 additional mole parts of ammonia were added and the reaction continued for 5 hours at 265°C. Conversion of 2-methyl-6-tert-butylphenol to 2-methyl-6-tert-butyl aniline was 34 per cent. Calculated yield of 2-methyl-6-tert-butyl aniline was about 98 per cent.

EXAMPLE 7

In a pressure reaction vessel was placed one mole part of 2-methyl-6-tert-butylphenol and 0.0045 mole part of palladium (5 weight per cent palladium on charcoal). Then, 3 mole parts of ammonia were added as 29 per cent aqueous ammonium hydroxide. The vessel was sealed and pressurized with hydrogen to 1,000 psig and heated to 200°C. Hydrogenation was continued until a total pressure drop of 820 psi was obtained. A sample was withdrawn and analyzed by gas chromatography at this point and found to be 72 per cent 2-methyl-6-tert-butylphenol and 20 per cent 2-methyl-6-tert-butyl cyclohexanone. The sealed vessel was then heated to 250°C and stirred at this temperature for 15 hours. The vessel was cooled and the contents distilled to give a 52.4 per cent conversion and 95.8 per cent yield of 2-methyl-6-tert-butyl aniline.

EXAMPLE 8

The procedure of Example 7 was repeated except the ammonium hydroxide was not added until after the hydrogenation. Instead, 50 parts of water were added prior to hydrogenation and the pressure drop was 400 psi. Conversion to 2-methyl-6-tert-butyl aniline was 54 per cent and yield was 98.7 per cent based on 2-methyl-6-tert-butylphenol.

EXAMPLE 9

In a pressure reaction vessel was placed 1.5 mole part of 2-methyl-6-tert-butylphenol and 0.0067 mole part of palladium (5 weight per cent palladium on charcoal). The vessel was pressurized to 180 psig with hydrogen and heated to 200°C over a 15 minute period. It was then cooled and 3.36 mole parts of ammonia (as 29 per cent aqueous ammonium hydroxide) were added. Gas chromatographic analysis of the mixture at this time showed it to contain 15.1 weight per cent 2-methyl-6-tert-butyl cyclohexanone, 80.4 weight per cent 2-methyl-6-tert-butylphenol and 0.5 weight per cent 2-methyl-6-tert-butyl aniline. The vessel was sealed and stirred at 250°C. After 5 hours the vessel contents analyzed 10.5 weight per cent 2-methyl-6-tert-butyl cyclohexanone, 38 weight per cent 2-methyl-6-tert-butylphenol and 46.6 weight per cent 2-methyl-6-tert-butyl aniline. These results show that very little change in the cyclohexanone content of the reaction mixture has occured. This demonstrates that the 2-methyl-6-tert-butyl aniline is being formed at the expense of 2-methyl-6-tert-butylphenol and that the 2-methyl-6-tert-butyl cylcohexanone serves a catalytic function.

EXAMPLE 10

In a pressure reaction vessel was placed 122 parts of 2,6-dimethylphenol, 176 parts of concentrated ammonium hydroxide and 9.5 parts of 5 per cent palladium on charcoal. The vessel was flushed with nitrogen, sealed and pressurized to 100 psig with hydrogen. It was then heated to 250°C while stirring and maintained at that temperature for 12 hours. The reaction mixture was cooled, diluted with benzene and filtered. Product was recovered by distillation. The conversion of the 2,6-dimethylphenol to 2,6-dimethylaniline was 78.6 per cent. After credit for recovered 2,6-dimethylphenol starting material, the actual yield was about 99 per cent.

EXAMPLE 11

In a pressure reaction vessel place one mole part of 2,6-dimethylphenol, 0.1 mole part of 2,6-dimethyl cyclohexanone, 0.007 mole part of platinum (0.1 weight per cent on silica-alumina support) and 3 mole parts of ammonia (as 29 per cent aqueous ammonium hydroxide). Seal the vessel and heat to 300°C and stir at this temperature for 4 hours. Cool and filter off the catalyst for recycle. Distill the filtrate to obtain the product 2,6-dimethyl aniline in good yield.

The above example can also be carried out using a solvent such as toluene.

EXAMPLE 12

In a pressure reaction vessel place one mole part of 2-naphthol, 0.05 mole part of cyclohexanone, 0.005 mole part of palladium (0.05 weight per cent on kielsguhr support) and 2 mole parts of aqueous ammonia. Seal the vessel and heat to 300°C. Stir at 300°–325°C for 8 hours and then cool and filter. Distill the filtrate to recover as the main product β-naphthyl amine.

EXAMPLE 13

In a pressure reaction vessel place one mole part of 2,4-di-tert-butylphenol, 0.2 mole part of tetralin and 0.007 mole part of palladium (5 weight per cent on charcoal support). Heat to 200°C and stir for one hour at that temperature. Cool and add 5 mole parts of ammonia (as 29 per cent aqueous ammonium hydroxide). Seal and heat to 275°C and stir at that temperature for 24 hours. Cool and filter to remove the palladium catalyst. Recover the product 2,4-di-tert-butyl aniline by distillation.

EXAMPLE 14

In a pressure reaction vessel place one mole part of o-cresol, 0.1 mole part of 1-methyl cyclohexanone, 0.007 mole part of palladium (5 weight per cent on charcoal support), and 2 mole parts of ammonium hydroxide. Seal the vessel and heat to 275°C and stir at this temperature for 8 hours. Cool, filter and distill to recover the product 2-methyl aniline.

The procedure of Example 9 is repeated in each of the following examples by replacing the 2-methyl-6-tert-butylphenol used in Example 9 with an equal mole amount of the designated hydroxy aromatics as follows.

| EXAMPLE | HYDROXY AROMATIC | AROMATIC AMINE PRODUCT |
|---|---|---|
| 15. | β-naphthol | β-naphthyl amine |
| 16. | p-cresol | p-methyl aniline |
| 17. | p-pentacontyl phenol | p-pentacontyl aniline |
| 18. | o-(α-methylbenzyl)phenol | o-(α-methylbenzyl) aniline |
| 19. | 2,6-dicyclohexylphenol | 2,6-dicyclohexyl aniline |
| 20. | 2,4,6-tri-tert-butyl-phenol | 2,4,6-tri-tert-butyl aniline |
| 21. | 7-hydroxy indene | 7-amino indene |
| 22. | 4,6-dibromo-7-hydroxy indene | 4,6-dibromo-7-amino indene |
| 23. | 4-hydroxy benzofuran | 4-amino benzofuran |
| 24. | 2-cyclooctyl-p-cresol | 2-cyclooctyl-4-methyl aniline |
| 25. | p-phenylphenol | p-phenyl aniline |
| 26. | p-(3,5-di-sec-heptyl-phenyl)phenol | p-(3,5-di-sec-heptylphenol)-aniline |
| 27. | o-(1-methylcyclohexyl)-phenol | o-(1-methylcyclohexyl)aniline |
| 28. | 2-sec-butyl-4,6-dinitro-phenol | 2-sec-butyl-4,6-dinitro aniline |
| 29. | 2,6-di-sec-butylphenol | 2,6-di-sec-butyl aniline |
| 30. | 2,6-diisopropylphenol | 2,6-diisopropyl aniline |
| 31. | 7-hydroxy indole | 7-amino indole |
| 32. | 7-hydroxy-4-nitro-isobenzofuran | 7-amino-4-nitro-isobenzofuran |
| 33. | 4-hydroxy-7-acetoxy indolenine | 4-amino-7-acetoxy indolenine |
| 34. | 7-hydroxy-4-methoxy-isothionaphthene | 7-amino-4-methoxy-isothionaphthene |
| 35. | 4-hydroxy-benzoisoxazole | 4-amino-benzoisoxazole |
| 36. | 7-hydroxy-4-iodo-benzoisoxazole | 7-amino-4-iodo-benzoisoxazole |
| 37. | 6-hydroxy coumarin | 6-amino coumarin |
| 38. | 6-hydroxy-8-fluoro-coumarin | 6-amino-8-flouorocoumarin |
| 39. | 2-methyl-α-naphthol | 2-methyl-α-naphthyl amine |
| 40. | 2-(α,α-dimethylbenzyl-α-naphthol | 2-(α,α-dimethylbenzyl)-α-naphthyl amine |
| 41. | 6,8-dichloro-β-naphthol | 6,8-dichloro-β-naphthyl amine |
| 42. | 2,4-dinitro-α-naphthol | 2,4-dinitro-α-naphthyl amine |
| 43. | 6-hydroxy quinoline | 6-amino quinoline |
| 44. | 4-hydroxy acenaphthene | 4-amino acenaphthene |
| 45. | 4-hydroxy-7-methyl-acenaphthene | 4-amino-7-methyl acenaphthene |
| 46. | 4-hydroxy-6,8-dinitro-acenaphthene | 4-amino-6,8-dinitro acenaphthene |
| 47. | 4-hydroxy-6,8-dibromo-acenaphthene | 4-amino-6,8-dibromo acenaphthene |
| 48. | 1-hydroxy fluorene | 1-amino fluorene |
| 49. | 1-hydroxy-2,4-di-sec-amyl fluorene | 1-amino-2,4-di-sec-amyl-fluorene |
| 50. | 2-hydroxy-6,8-difluoro fluorene | 2-amino-6,8-difluoro fluorene |
| 51. | 1-hydroxy-dibenzo-pyrrol | 1-amino-dibenzopyrrol |
| 52. | 1-hydroxy-2-ethyl-dibenzopyrrol | 1-amino-2-ethyl-dibenzopyrrol |
| 53. | 1-hydroxy-2,4-diisopropyl-dibenzopyrrol | 1-amino-2,4-diisopropyl di-benzopyrrol |
| 54. | α-hydroxy anthracene | α-amino anthracene |
| 55. | α-hydroxy-2-phenyl anthracene | α-amino-2-phenyl anthracene |
| 56. | α-hydroxy-2-(2,4-di-sec-heptylphenyl)- | α-amino-2-(2,4-di-sec-heptylphenyl)anthracene |
| 57. | β-hydroxy anthracene | β-amino anthracene |
| 58. | 9-hydroxy anthracene | 9-amino anthracene |
| 59. | α-hydroxy-5-dodecyl anthracene | α-amino-5-dodecyl anthracene |
| 60. | α-hydroxy-5-triacontyl anthracene | α-amino-5-triacontyl anthracene |
| 61. | α-hydroxy-8-pentacontyl | α-amino-8-pentacontyl anthracene |

-continued

| EX-AMPLE | HYDROXY AROMATIC | AROMATIC AMINE PRODUCT |
|---|---|---|
| 62. | α-hydroxy-2,4-dinitro anthracene | α-amino-2,4-dinitro anthracene |
| 63. | α-hydroxy-2,4-dichloro anthracene | α-amino-2,4-dichloro anthracene |
| 64. | 3-hydroxy phenanthrene | 3-amino phenanthrene |
| 65. | 3-hydroxy-2-ethoxy phenanthrene | 3-amino-2-ethoxy phenanthrene |
| 66. | 3-hydroxy-7-chloro phenanthrene | 3-amino-7-chloro phenanthrene |
| 67. | 3-hydroxy-8-methyl phenanthrene | 3-amino-8-methyl phenanthrene |
| 68. | 3-hydroxy-5-nitro phenanthrene | 3-amino-5-nitro phenanthrene |
| 69. | 2-hydroxy-8-(α-methylbenzyl)phenanthrene | 2-amino-8-(α-methylbenzyl)-phenanthrene |
| 70. | 8-hydroxy phenanthrene | 8-amino phenanthrene |
| 71. | 8-hydroxy-cyclopentane phenanthrene | 8-amino-cyclopentano phenanthrene |
| 72. | 1-hydroxy xanthene | 1-amino xanthene |
| 73. | 1-hydroxy phenazine | 1-amino phenazine |
| 74. | 3-ethyl-4,5,7-trihydroxy coumarin | 3-ethyl-4,5,7-triamino coumarin |
| 75. | 3-n-propyl-4,7,8-tri-hydroxy coumarin | 3-n-propyl-4,7,8-triamino coumarin |
| 76. | 3-n-butyl-4,5,7-tri-hydroxy coumarin | 3-n-butyl-4,5,7-triamino coumarin |
| 77. | 3-n-butyl-4,7,8-tri-hydroxy coumarin | 3-n-butyl-4,7,8-triamino coumarin |
| 78. | 3-phenyl-4,7,8-tri-hydroxy coumarin | 3-phenyl-4,7,8-triamino coumarin |
| 79. | 3-(1-naphthylmethyl)-4,5,7-trihydroxy coumarin | 3-(1-naphthylmethyl)-4,5,7-triamino coumarin |
| 80. | 3-(1-naphthylmethyl)-4,7,8-trihydroxy coumarin | 3-(1-naphthylmethyl)-4,7,8-triamino coumarin |
| 81. | 3-[2(β-pyridyl)ethyl]-4,5,7-trihydroxy coumarin | 3-[2(β-pyridyl)ethyl]-4,5,7-triamino coumarin |
| 82. | 4,4'-methylenebis(2,6-dimethylphenol) | 4,4'-methylenebis(2,6-dimethyl aniline) |
| 83. | 4,4'-bis(2,6-dimethyl-phenol | 4,4'-bis(2,6-dimethyl aniline) |

Other polyhydroxy aromatics can be used in the process such as hydroquinones, 2,6-di-tert-butyl-hydroquinones, pyrogallol, phloroglucinol, and the like.

According to another preferred embodiment of the invention the cyclohexanone used as a co-catalyst is obtained by recycling a distillation fraction from a prior process carried out in accordance with the described procedure. The distillation fraction which is recycled is the fraction which contains the reduced products of the hydroxy aromatic starting material. A large amount of these reduced products is the cyclohexanone which corresponds to the reduced hydroxy aromatic initially charged. Cyclohexanols and cyclohexyl amines are also included in the reduced product fraction in which the cyclohexyl portion corresponds in structure to the cyclohexyl portion of the cyclohexanone. For example, in the case where the initial hydroxy aromatic is 2,6-dimethyl phenol the reduced fraction recovered for recycle will usually contain about 20–50 weight per cent of 2,6-dimethylcyclohexanone, about 5–15 weight per cent of 2,6-dimethylcyclohexanol and about 30–60 weight per cent of 2,6-dimethylcyclohexyl amine. Under the described reaction conditions the cyclohexanol is believed to enter into a redox reaction with the phenol starting material to form additional cyclohexanone so in the described reaction system it is the equivalent of a cyclohexanone. Likewise, the cyclohexyl amine can enter into a redox reaction to form aromatic amine, or hydrolyze to form cyclohexanol. The reduced products containing the cyclohexanone, cyclohexanol and cyclohexyl amine or their derivatives corresponding to the starting hydroxy aromatic can be removed for recycle as a single distillation fraction. This fraction constitutes most of the material which distills at a boiling point lower than the hydroxy aromatic starting material and aromatic amine product.

This embodiment of employing a reduced products fraction as the co-catalyst in a subsequent operation is possible because very little of the cyclohexanone is consumed during the process. This permits its recovery, thus conserving phenol values.

The reduced fraction is readily obtained for recycle during product recovery. For example, after first filtering off the metal-containing hydrogen transfer catalysts (e.g., palladium), the liquid reaction product is subjected to distillation to recover the desired aromatic amine product. During this distillation the reduced product is isolated for recycle as the distillation fraction which boils below the hydroxy aromatic starting material and aromatic amine. Good results are obtained by adding about 0.05–0.5 mole parts of the reduced fraction to one mole part of hydroxy aromatic containing palladium catalyst and then reacting the mixture with ammonia. This preferred embodiment of the invention is illustrated by the following examples.

EXAMPLE 84

In a 600 ml autoclave was placed 140.4 grams of 2,6-dimethylphenol and 11 grams of 5% palladium on charcoal. The autoclave was sealed and pressurized to 400 psig with hydrogen and heated. At about 90°C, pressure drop started. Heating was continued to 180°C and the reaction then cooled and vented. About 16% of the phenol starting material was reduced to reduced products, mainly 2,6-dimethyl cyclohexanone. Then 135 grams of 29% aqueous ammonia was added. The autoclave was flushed with hydrogen, sealed, and heated to 250°C. It was stirred at this temperature for 4 hours and then cooled and filtered. Then 6.75 grams of NaCl was added to the filtrate to aid in separation of the aqueous phase which was removed. Gas chromatographic analysis of the organic phase of the reaction mixture showed it to contain:

| | |
|---|---|
| 2,6-dimethyl aniline | 73.66% |
| 2,6-dimethylphenol | 7.73% |
| reduced products[1] | 14.25% |
| m-xylene | 4.37% |

[1]Mainly 2,6-dimethylcyclohexanone plus lesser amounts of 2,6-dimethylcyclohexanol and 2,6-dimethylcyclohexyl amine.

This mixture was distilled at atmospheric pressure to recover:

| | |
|---|---|
| reduced products | b.p. 165–175°C |
| 2,6-dimethylphenol | b.p. 211–213°C |
| 2,6-dimethylaniline | b.p. 215–217°C |

EXAMPLE 85

This experiment utilizes recycled reduced product as the co-catalyst.

To the autoclave used in Example 84 was charged 120 grams 2,6-dimethylphenol, 20 grams of reduced products obtained as described in Example 84, 135 grams of 29% aqueous ammonia and 11 grams of 5% palladium on charcoal. The autoclave was flushed with hydrogen, sealed, and heated to 250°C. After stirring 4 hours at this temperature it was cooled and vented. It was filtered and the aqueous phase removed as in Example 84, and the organic phase analyzed by VPC to contain:

| | |
|---|---|
| 2,6-dimethyl aniline | 66.32% |
| 2,6-dimethylphenol | 17.18% |
| reduced products | 12.63% |
| m-xylene | 3.87% |

The above example illustrates how a recycled distillation fraction containing the reduced products can function very nicely as the cyclohexanone co-catalyst.

It is sometimes beneficial to combine use of recycled reduced products and hydrogenation to make up for any loss in reduced products during recycle. The following example illustrates this.

EXAMPLE 86

In a 600 ml autoclave was placed 126.4 grams of 2,6-dimethylphenol, 14 grams of reduced products obtained as in Example 84, and 11 grams of 5% palladium on charcoal. The vessel was flushed with hydrogen and pressurized with hydrogen to 130 psig (0.17 mole hydrogen required). The autoclave was heated to 175°C and then cooled and vented. Then 135 grams of 29% aqueous ammonia was added. The autoclave was sealed and heated to 250°C and stirred at this temperature for 4 hours, following which it was cooled. The contents were filtered to remove palladium catalyst and the aqueous phase removed from the filtrate. The organic phase analyzed by VPC as follows:

| | |
|---|---|
| 2,6-dimethyl aniline | 72.34% |
| 2,6-dimethylphenol | 7.23% |
| reduced products | 13.23% |
| m-xylene | 7.17% |

A further advantage of the two-stage process utilizing at least some hydrogenation is that it permits recycle of the palladium catalyst with little loss in activity. When palladium catalyst is recycled and employed in a one-stage process (i.e., the process in which the hydroxy aromatic and aqueous ammonia are both charged at the start of the reaction) considerable loss in activity is observed. However, in the two-stage process in which the hydroxy aromatic containing the recycled catalyst is hydrogenated prior to adding ammonia there is little loss in catalyst activity. This is shown in the following examples.

EXAMPLE 87

In the autoclave used in the previous example was placed 126.4 grams of 2,6-dimethylphenol, 14 grams of reduced product and 12.2 grams of recycled charcoal-supported palladium catalyst from Example 86, which had been washed with acetone and dried. The vessel was pressurized to 130 psig with hydrogen (0.17 mole) and heated to 210°C. Hydrogen uptake started at about 150°C. The autoclave was cooled, vented, and then 135 grams of 29% aqueous ammonia added. It was then sealed and heated to 250°C and stirred at this temperature for 4 hours. Tha autoclave was again cooled and the contents filtered to remove catalyst. The aqueous phase was separated and the organic phase analyzed by VPC as follows:

| | |
|---|---|
| 2,6-dimethyl aniline | 70.48% |
| 2,6-dimethylphenol | 10.56% |
| reduced products | 14.27% |
| m-xylene | 4.67% |

As the above results, show, the palladium catalyst can be recycled following the two-stage method with but little loss in activity.

Reduced fractions obtained from other amination reactions carried out in accordance with the present process can also be recycled to a subsequent run as the cyclohexanone co-catalyst. For example, when the starting hydroxy aromatic is 2-methyl-6-tert-butylphenol the reduced fraction available for recycle consists mainly of a mixture of 2-methyl-6-tert-butylcyclohexanone, 2-methyl-6-tert-butylcyclohexanol and 2-methyl-6-tert-butylcyclohexyl amine. With 2,4,6-trimethylphenol the reduced fraction consists mainly of 2,4,6-trimethylcyclohexanone, 2,4,6-trimethylcyclohexanol and 2,4,6-trimethylcyclohexyl amine. With 2-methyl-6-tert-(α,α-dimethylbenzyl)phenol the reduced fraction is mainly 2-methyl-6-(α,α-dimethylbenzyl)cyclohexanone, 2-methyl-6-(α,α-dimethylbenzyl)-cyclohexanol and 2-methyl-6-(α,α-dimethylbenzyl)cyclohexyl amine. All of these reduced fractions can be recycled to subsequent runs as the cyclohexanone co-catalyst. It is readily seen that the reduced fractions consist mainly of the cyclohexyl ketone, alcohol and amine corresponding in structure to the starting hydroxy aromatic, but having the phenolic benzene ring reduced to a cyclohexane ring.

The amines made by this process are useful for a variety of purposes. They are intermediates for antioxidants, antiozonants, dyes, herbicides and insecticides.

The lower molecular weight gasoline-soluble aniline derivatives are useful antiknock agents for spark-ignited internal combustion engines (Ind. Eng. Chem., 47, page 2141, 1955). For example, 2,4-dimethyl aniline made from 2,4-dimethylphenol and ammonia is also a very effective antiknock agent. In this use, they are added to a liquid hydrocarbon fuel of the gasoline boiling range in an antiknock amount, generally from 0.25 to 1 per cent.

In U.S. Pat. No. 3,322,810 is described certain 2,6-dialkyl isothiocyanates which are useful as pesticides. The isothiocyanates are made by reacting carbon disulfide with a 2,6-dialkyl aniline. These anilines are readily made by the present process. For example, 2,6-dimethyl aniline is made in good yield from the corresponding 2,6-dimethylphenol, as shown in Example 11.

The compounds made by this invention are also intermediates in the manufacture of polyurethanes. These polymers are made by reacting aromatic diisocyanates with polyhydroxy compounds. The diisocyanates are in turn made by the reaction of diamino aromatics with phosgene. The present invention provides a good process for the preparation of the diamino aromatic from the corresponding dihydroxy aromatic. For example, 4,4'-diisocyanato-3,3',5,5'-tetramethyl diphenylmethane is readily made by either (1) reacting 4,4'-dihydroxy-3,3',5,5'-tetramethyl diphenylmethane with ammonia at 200°–400°C, or (2) reacting 2,6-dimethylphenol with ammonia to form 2,6-dimethyl aniline and subsequently coupling this aniline at the 4 position through a methylene bridge by reaction with formaldehyde.

I claim:

1. In a process for converting a hydroxy aromatic starting material to the corresponding aromatic amine, said process comprising reacting said hydroxy aromatic with ammonia in the presence of a catalyst at a temperature of about 200°–400°C, the improvement wherein said catalyst is a Group VIII metal catalyst in combination with from about 0.05 to about 0.5 moles of a saturated cyclohexanone co-catalyst per mole of said hydroxy aromatic.

2. An improved process of claim 1 wherein said catalyst is palladium supported on a catalyst support.

3. An improved process of claim 2 wherein said hydroxy aromatic is an alkyl-substituted mononuclear phenol.

4. An improved process of claim 3 wherein said alkyl-substituted mononuclear phenol is an ortho-alkyl-substituted phenol.

5. An improved process of claim 4 wherein said ortho-alkyl-substituted phenol is a 2,6-dialkylphenol.

6. An improved process of claim 5 wherein said 2,6-dialkylphenol is 2,6-dimethylphenol.

7. An improved process of claim 6 wherein said cyclohexanone is 2,6-dimethyl cyclohexanone.

8. An improved process of claim 5 wherein said 2,6-dialkylphenol is a 2-methyl-6-tert-alkylphenol.

9. An improved process of claim 8 wherein said 2-methyl-6-tert-alkylphenol is 2-methyl-6-tert-butylphenol.

10. An improved process of claim 9 wherein said cyclohexanone is 2-methyl-6-tert-butyl-cyclohexanone.

11. An improved process of claim 5 wherein said 2,6-dialkylphenol is a 2,6-di-tert-alkylphenol.

12. An improved process of claim 11 wherein said 2,6-di-tert-alkylphenol is 2,6-di-tert-butylphenol.

13. An improved process of claim 2 wherein said cyclohexanone co-catalyst is the reduced product of said hydroxy aromatic formed by reducing a portion of said hydroxy aromatic with hydrogen.

14. An improved process of claim 13 wherein said reduced product of said hydroxy aromatic is formed in a first stage by reacting said hydroxy aromatic containing said palladium catalyst with hydrogen and thereafter, in a second stage, adding said ammonia and reacting at 200°–400°C.

15. An improved process of claim 14 wherein said hydroxy aromatic is 2,6-dimethylphenol.

16. An improved process of claim 14 wherein said hydroxy aromatic is 2-methyl-6-tert-butylphenol.

17. An improved process of claim 2 wherein said cyclohexanone co-catalyst is a distillation fraction from a prior process carried out in accordance with claim 2, said distillation fraction consisting essentially of said cyclohexanone and a cyclohexanol and a cyclohexyl amine wherein the cyclohexyl portion of said cyclohexanol and said cyclohexyl amine corresponds to the cyclohexyl portion of said cyclohexanone.

18. An improved process of claim 17 adapted for making 2,6-dimethylaniline, said process comprising adding a palladium catalyst and said distillation fraction consisting essentially of 2,6-dimethylcyclohexanone, 2,6-dimethylcyclohexanol and 2,6-dimethylcyclohexylamine to 2,6-dimethylphenol and reacting this mixture with aqueous ammonia at a temperature of about 200°–400°C, said distillation fraction being a distillation fraction obtained from a previous reaction of 2,6-dimethylphenol with ammonia in contact with a palladium catalyst and 2,6-dimethylcyclohexanone co-catalyst.

19. An improved process of claim 17 adapted for making 2-methyl-6-tert-butylaniline, said process comprising adding a palladium catalyst and said distillation fraction consisting essentially of 2-methyl-6-tert-butylcyclohexanone, 2-methyl-6-tert-butylcyclohexanol and 2-methyl-6-tert-butylcyclohexylamine to 2-methyl-6-tert-butylphenol and reacting this mixture with aqueous ammonia at a temperature of about 200°–275°C, said distillation fraction being a distillation fraction obtained from a previous reaction of 2-methyl-6-tert-butylphenol with ammonia in contact with a palladium catalyst and 2-methyl-6-tert-butylcyclohexanone co-catalyst.

20. A process for making 2,6-dimethylaniline, said process comprising adding a palladium catalyst to 2,6-dimethylphenol, hydrogenating said 2,6-dimethylphenol with about 0.1–1.0 moles of hydrogen per mole of 2,6-dimethylphenol to reduce a portion of said 2,6-dimethylphenol, adding about 1–4 moles of ammonia per mole of initial 2,6-dimethylphenol, heating the mixture in a sealed vessel at 200°–400°C to convert said 2,6-dimethylphenol to 2,6-dimethylaniline, and recovering said 2,6-dimethylaniline.

21. A process for making 2,6-dimethylaniline, said process comprising adding a palladium catalyst to 2,6-dimethylphenol, adding as a co-catalyst a distillation fraction of reduced products consisting essentially of a mixture of 2,6-dimethylcyclohexanone, 2,6-dimethylcyclohexanol and 2,6-dimethylcyclohexylamine, said distillation fraction being obtained from a previous reaction carried out in the same manner, adding about 1–4 moles of ammonia per mole of said 2,6-dimethylphenol, heating the mixture in a sealed vessel at 200°–400°C to convert said 2,6-dimethylphenol to 2,6-dimethylaniline, distilling the resultant mixture to obtain distillation fractions of reduced products and 2,6-dimethylaniline product, said reduced products having a boiling point below 2,6-dimethylphenol and 2,6-dimethylaniline and consisting essentially of a mixture of 2,6-dimethylcyclohexanone, 2,6-dimethylcyclohexanol and 2,6-dimethylcyclohexylamine and recycling said reduced products as the co-catalyst in a subsequent reaction carried out in the same manner.

22. A process of claim 21 wherein hydrogen is reacted with the initial mixture of 2,6-dimethylphenol, palladium catalyst and reduced products co-catalyst in an amount sufficient to adjust the total amount of reduced products to about 0.05–0.5 moles per mole of 2,6-dimethylphenol.

23. A process for making 2-methyl-6-tert-butylaniline, said process comprising adding a palladium catalyst to 2-methyl-6-tert-butylphenol, hydrogenating said 2-methyl-6-tert-butylphenol with about 0.1–1 moles of hydrogen per mole of 2-methyl-6-tert-butylphenol to reduce a portion of said 2-methyl-6-tert-butylphenol, adding about 1–4 moles of ammonia per mole of initial 2-methyl-6-tert-butylphenol and heating the mixture in a sealed vessel at 200°–275°C to convert said 2-methyl-6-tert-butylphenol to 2-methyl-6-tert-butylaniline and recovering said 2-methyl-6-tert-butylaniline.

24. A process for making 2-methyl-6-tert-butylaniline, said process comprising adding a palladium catalyst to 2-methyl-6-tert-butylphenol, adding as a co-catalyst a distillation fraction of reduced products consisting essentially of a mixture of 2-methyl-6-tert-butylcyclohexanone, 2-methyl-6-tert-butylcyclohexanol and 2-methyl-6-tert-butylcyclohexylamine, said distillation fraction being obtained from a previous reaction carried out in the same manner, adding about 1–4 moles of ammonia per mole of said 2-methyl-6-tert-butylphenol, heating the mixture in a sealed vessel at 200°–275°C to convert said 2-methyl-6-tert-butylphenol to 2-methyl-6-tert-butylaniline, distilling the resultant mixture to obtain distillation fractions of reduced products and 2-methyl-6-tert-butylaniline product, said reduced products having a boiling point below 2-methyl-6-tert-butylphenol and 2-methyl-6-tert-butylaniline and consisting essentially of a mixture of 2-methyl-6-tert-butylcyclohexanone, 2-methyl-6-tert-butylcyclohexanol and 2-methyl-6-tert-butylcyclohexylamine and recycling said reduced products as the co-catalyst in a subsequent reaction carried out in the same manner.

25. A process of claim 24 wherein hydrogen is reacted with the initial mixture of 2-methyl-6-tert-butylphenol, palladium catalyst and reduced products co-catalyst in an amount sufficient to adjust the total amount of reduced products to about 0.05–0.5 moles per mole of 2-methyl-6-tert-butylphenol.

* * * * *